United States Patent [19]

Saville

[11] Patent Number: Plant 5,484

[45] Date of Patent: Jun. 4, 1985

[54] ROSE PLANT

[75] Inventor: F. Harmon Saville, Rowley, Mass.

[73] Assignee: Nor'East Miniature Roses, Inc., Rowley, Mass.

[21] Appl. No.: 556,268

[22] Filed: Nov. 30, 1983

[51] Int. Cl.[3] ..... A01H 5/00

[52] U.S. Cl. ..... Plt./10

[58] Field of Search ..... Plt./7, 10

*Primary Examiner*—Robert E. Bagwill

*Attorney, Agent, or Firm*—Vincent G. Gioia

[57] ABSTRACT

A new miniature rose variety of bright red coloring with Naples yellow colored flower centers which are long lasting on the plant and as a cut flower.

1 Drawing Figure

The present invention relates to a new and distinct variety of rose plant of the miniature rose class, which was originated by my crossing as seed parent the rose known as "Poker Chip" (U.S. Plant Pat. No. 4,582) and the rose known as "Zinger" (U.S. Plant Pat. No. 4,293) as pollen parent. The varietal denomination of this new variety is "Savalot".

Among the novel characteristics possessed by this new variety which distinguish it from its parents and all other varieties of which I am aware are its bright red flowers with Naples yellow flower centers resulting from yellow coloring of petals toward point of petal attachment and which are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46B" is plate 46B of The Royal Horticultural Society Colour Chart.

Parentage: Seedling.

*Seed parent.*—"Poker Chip".

*Pollen parent.*—"Zinger".

Class: Miniature.

The following observations are made of specimens grown outdoors in Essex County, Mass., during the month of October.

FLOWER

Blooming Habit: Near continuous.

Bud:

(1) *Size.*—Medium.

(2) *Form.*—Ovate, short, becoming urn shaped as petals unfurl.

(3) *Color.*—When sepals first divide — currant red near 46B until sepals begin to fall and lower section of petal undersurface is seen which shows the red coloring washing into 11A to 11B and then becoming 11A to 11B at lowermost section of petal undersurface (4) *Sepals.*—Long than bud, slightly foliated.

(5) *Peduncle.*—Length — 1 to $1\frac{1}{4}$ inches. Aspect — straight. Strength — erect. Color — near 146C.

Bloom:

(1) *Size.*—Average size when fully expanded — about $1\frac{1}{4}$ to $1\frac{1}{2}$ inches (2) *Borne.*—Singly and small sprays.

(3) *Form.*—High centered at first, becoming flat.

(4) *Petalage.*—Number of petals under normal conditions — about 20 to 25.

(5) *Color.*—As currant red buds 46B unfurl, Naples yellow 11A to 11B coloring of lower petal section is revealed. Upon opening further, at about $\frac{1}{2}$ open stage, similar Naples yellow coloring on petal top surface at lower $\frac{1}{4}$ to 1/5 section of the petal is visible. Also, red coloring of flower bud lightens to near 44A, when fully open. When fully open, Naples yellow coloring of the petals toward the point of petal attachment becomes eye catching which together with slightly darker yellow stamens produces an attractive bicolor effect. Partially open blooms show some lighter tonality mottling on the petal undersurface and petal undersurface is generally lighter toned than petal top surface.

Petals:

(1) *Texture.*—Thick.

(2) *Appearance.*—Inside — velvety, outside — satiny.

(3) *Form.*—Fan shaped.

(4) *Arrangement.*—Regularly arranged, shingle-like.

(5) *Petaloids in center.*—Few.

(6) *Persistence.*—Drop off cleanly.

(7) *Fragrance.*—Slight.

(8) *Lasting quality.*—Very long lasting on plant and as cut flower.

REPRODUCTIVE ORGANS

Stamens, filaments and anthers:

(1) *Arrangement.*—Regularly arranged around styles.

(2) *Color.*—Near 24B.

Pollen:

*Color.*—Near 24A.

Styles: Medium length.

Stigmas:

*Color.*—Near 1D.

Hips:

*Shape.*—Globular.

*Size.*—About $\frac{3}{4}$ inch.

*Color.*—Orange.

*Do seeds protrude?*—Occasionally.

PLANT

Form: Compact, bushy.

Growth: Vigorous.

*Height attained.*—About 12 to 16 inches.

Foliage: Compound 5 to 7 leaflets.

(1) *Size.*—Medium.

(2) *Quantity.*—Abundant.

(3) *Color.*—New foliage.

Upper side — near to 146B. Under side — near to 138B. Old foliage. Upper side — near 137A. Under side — near 138B.

(4) *Shape.*—Oval.

(5) *Texture.*—Upper side is slightly glossy and under side is dull.

(6) *Edge.*—Serrated.

(7) *Serration.*—Serrate.

(8) *Leaf stem.*—Color — near to 146B. Under side — near 144B.

(9) *Stipules.*—Medium, slightly bearded.

(10) *Resistance to disease.*—Blackspot — average. Mildew — average. Rust — average.

Wood:

(1) *New wood.*—Color — near 143A. Bark — smooth.

(2) *Old wood.*—Color — near 146B. Bark — rough.

Thorns:

(1) *Thorns.*—Quantity (main stalk): ordinary. On laterals from stalk — average. Form — Long, straight, thin. Length — medium. Color — near 186C. Position — irregular.

(2) *Prickles.*—None.

Winter hardiness: Requires ordinary protection in extreme climates.

I claim:

1. A new and distinct variety of rose plant of the miniature rose class, substantially as shown and described, characterized particularly by bright red buds which upon opening reveal bicolored petals of red and Naples yellow toward point of petal attachment and display yellow centers amid red colored petals at full open bloom, flowers are very long lasting on the plant and after cutting.

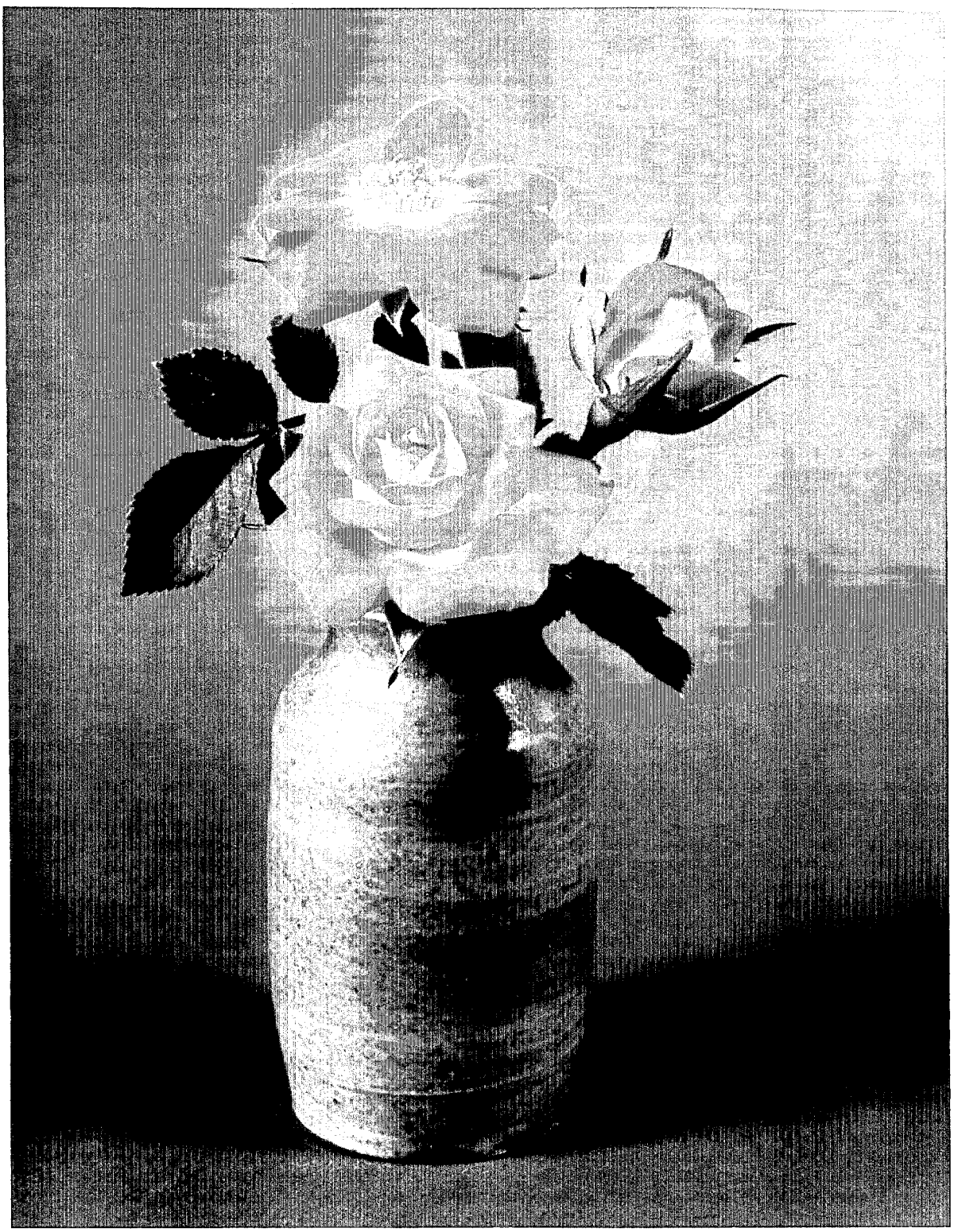

* * * * *